United States Patent [19]

Masaki et al.

[11] Patent Number: 5,070,196
[45] Date of Patent: Dec. 3, 1991

[54] ALKYLENEDIAMINE DERIVATIVES

[75] Inventors: Mitsuo Masaki, Chiba; Masaru Satoh, Koshigaya; Naoya Moritoh, Kuki; Koichi Hashimoto, Tokyo; Toshiro Kamishiro, Misato; Haruhiko Shinozaki, Oomiya, all of Japan

[73] Assignee: Nippon Chemiphar Co., Ltd., Tokyo, Japan

[21] Appl. No.: 562,422

[22] Filed: Aug. 1, 1990

Related U.S. Application Data

[63] Continuation of Ser. No. 228,343, Aug. 1, 1988, abandoned, which is a continuation-in-part of Ser. No. 165,351, Feb. 29, 1988, abandoned, which is a continuation of Ser. No. 9,170, Jan. 30, 1987, abandoned.

[30] Foreign Application Priority Data

| Feb. 1, 1986 | [JP] | Japan | 61-20497 |
| Feb. 1, 1986 | [JP] | Japan | 61-20498 |
| Aug. 1, 1987 | [JP] | Japan | 62-193201 |
| Aug. 1, 1987 | [JP] | Japan | 62-193203 |

[51] Int. Cl.$^5$ .................. C07D 225/04; C07D 233/04; C07D 211/14; C07D 207/04
[52] U.S. Cl. ..................... 540/450; 540/609; 546/246; 548/569
[58] Field of Search ............. 546/246; 548/569; 540/450, 609

[56] References Cited

U.S. PATENT DOCUMENTS 3,371,093  2/1968  Zenitz et al. .......... 546/246 X
3,712,896  1/1973  Tilford et al. ............ 546/246

FOREIGN PATENT DOCUMENTS 177245  4/1986  European Pat. Off.

OTHER PUBLICATIONS

E. Szarvasi et al., *Bull. Soc. Chem. France* 6 (1966), 1838–1846.

*Primary Examiner*—Mary C. Lee
*Assistant Examiner*—Joseph K. McKane
*Attorney, Agent, or Firm*—Sixbey, Friedman, Leedom & Ferguson

[57] ABSTRACT

Novel alkylenediamine derivatives effectively employable as glutamate blockers have the formula (I) or (II):

$$R^1-(CH_2)_m-CH(R^2)-(CH_2)_n-NH-(CH_2)_p-N\langle ring\ with\ (CH_2)_q,\ R^3,\ R^4,\ R^5\rangle \quad (I)$$

$$R^6-(CH_2)_k-N(R^7)-(CH_2)_i-N\langle ring\ with\ (CH_2)_j,\ R^8,\ R^9,\ R^{10}\rangle \quad (II)$$

wherein each of $R^1$ and $R^6$ is an aliphatic hydrocarbon group, an alicyclic hydrocarbon group, an aryl group, or an aralkyl group; each of $R^2$ and $R^7$ is an aliphatic hydrocarbon group, an alkoxy group, an aliphatic hydrocarbon group containing an ester bonding, an aliphatic hydrocarbon group containing an ether bonding, or an aryloxy group; each of $R^3$, $R^4$, $R^5$, $R^8$, $R^9$ and $R^{10}$ is hydrogen, an alkyl group, an alkoxy group, an acyloxy group, an aryl group, an aralkyl group, hydroxyl, a hydroxylalkyl group, halogen, nitrile, nitro, amino, carbamoyl or alkoxycarbonyl; and each of m and n is an integer of 0–3 (m+n does not exceed 3); k is an integer of 1–4; each of p and i is an integer of 2–13; and each of q and j is an integer of 4–7.

17 Claims, No Drawings

ALKYLENEDIAMINE DERIVATIVES

This application is a continuation of Ser. No. 07/228,343, filed Aug. 1, 1988, now abandoned, which was a continuation-in-part of Ser. No. 07/165,351 filed Feb. 29, 1988, now abandoned, which was a continuation of Ser. No. 07/009,170, now abandoned.

BACKGROUND OF THE INVENTION

1. Field of the Invention

The present invention relates to novel alkylenediamine derivatives. The alkylenediamine derivatives of the invention are favorably employable as glutamate blockers.

2. Description of Prior Art

It is generally accepted that glutamate serves as an excitatory transmitter in the Crustacea. Further, it is also considered that glutamate is a potent candidate of the excipitory transmitter even in the central nervous system of mammals.

There is known γ-methylester of glutamic acid as a glutamate blocker which is effective to inhibit the above-mentioned functions of glutamate. However, the glutamate blocking function of the γ-methylester of glutamic acid is observed only when it is employed at high concentrations such as $10^{-2}$ m to $10^{-3}$M. Accordingly, the γ-methylester is not satisfactory from the viewpoint of practical employment as the glutamate blocker.

It is further reported that Diltiazem and Caroberine also show inhibition against the functions of glutamate :see "Seitai no Kagaku" in Japanese Language, 30(2): 8291, 1979. However, the inhibitory function of these compounds is weak, as compared with other blockers employed in other transmission systems, such as anticholinergic agents against acetylcoline and antihistamines against histamine. For instance, at dose of $2 \times 10^{-4}$ Diltiazem and Caroberine both are effective only such low level as to inhibit approx. 30% of depolarization induced in the case of applying glutamic acid $(1 \times 10^{-4}$ M) to the opener muscle of the first walking leg of the crayfish. Further, the action provided by these known compounds is not selective.

Furthermore, it has been reported that aminoalcohol derivatives such as 5-methyl-1-phenyl-2-(3-piperidinopropylamino)hexan-1-ol show the glutamate blocking function. However, the glutamate blocking functions of these amino-alcohol derivatives are not sufficiently high if the administration is made at a low level.

SUMMARY OF THE INVENTION

An object of the present invention is to provide novel alkylenediamine derivatives which effectively function as glutamate blockers.

There is provided by the present invention an alkylenediamine derivative having the following formula (I):

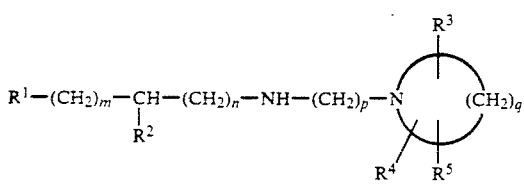

wherein $R^1$ is a straight or branched chain aliphatic hydrocarbon group containing 3-8 carbon atoms, an alicyclic hydrocarbon group containing 5-8 carbon atoms, an aryl group, or an aralkyl group having an alkyl group containing 1-4 carbon atoms; $R^2$ is a straight or branched chain aliphatic hydrocarbon group containing 3-11 carbon atoms, an alkoxy group containing 3-11 carbonatoms, an aliphatic hydrocarbon group containing an ester bonding and 3-11 carbon atoms, an aliphatic hydrocarbon group containing an ether bonding and 3-11 carbon atoms, or an aryloxy group; each of $R^3$, $R^4$ and $R^5$ independently is hydrogen, a saturated or unsaturated straight or branched chain alkyl group containing 1-6 carbon atoms, an alkoxy group containing 1-6 carbon atoms, an acyloxy group containing 1-6 carbon atoms, an aryl group which may have at least one substituent, an aralkyl group having an alkyl group of 1-5 carbon atoms which may have at least one substituent, hydroxyl, a hydroxylalkyl group having an alkyl group of 1-3 carbon atoms, halogen, nitrile, nitro, amino, carbamoyl or alkoxycarbonyl having an alkyl group of 1-5 carbon atoms; and each of m and n is an integer of 0 to 3, provided that m + n does not exceed 3; p is an integer of 2 to 13; and q is an integer of 4 to 7.

The present invention also provides an alkylenediamine derivative having the following formula (II):

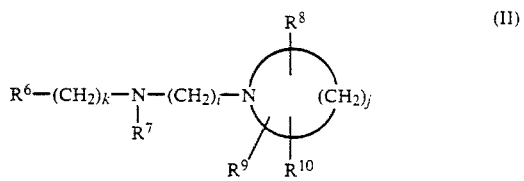

wherein $R^6$ is a straight or branched chain aliphatic hydrocarbon group containing 3-8 carbon atoms, an alicyclic hydrocarbon group containing 5-8 carbon atoms, an aryl group, or an aralkyl group having an alkyl group containing 1-4 carbon atoms; $R^7$ is a straight or branched chain aliphatic hydrocarbon group containing 3-11 carbon atoms, an aliphatic hydrocarbon group containing an ester bonding and 3-11 carbon atoms, an aliphatic hydrocarbon group containing an ether bonding and 3-11 carbon atoms, or an aralkyl group having an alkyl group containing ether bonding and 2-5 carbon atoms; each of $R^8$, $R^9$ and $R^{10}$ independently is hydrogen, a saturated or unsaturated straight or branched chain alkyl group containing 1-6 carbon atoms, an alkoxy group containing 1-6 carbon atoms, an acyloxy group containing 1-6 carbon atoms, an aryl group which may have at least one substituent, an aralkyl group having an alkyl group of 1-5 carbon atoms which may have at least one substituent, hydroxyl, a hydroxyalkyl group having an alkyl group of 1-3 carbon atoms, halogen, nitrile, nitro, amino, carbamoyl or alkoxycarbonyl having an alkyl group of 1-5 carbon atoms; k is an integer of 1 to 4; i is an integer of 2 to 13; and j is an integer of 4 to 7.

DETAILED DESCRIPTION OF THE INVENTION

The alkylenediamine derivative of the present invention is particularly useful as glutamate blocker. The glutamate blocking action of the alkylenediamine derivative of the invention is prominently high as much as 10 to 100 times or more, as compared with the actions provided by the known glutamate blockers such as γ-methylester of glutamic acid, Diltiazem, and Caroberine.

It is known that convulsion is caused when glutamic acid is injected into brain of mammal. Accordingly, the alkylenediamine derivative of the present invention showing prominent glutamate blocking action is of value as pharmaceutical for neuriatria caused by unbalanced nervous system or abnormal exasperation of muscular pulse.

Further, the alkylenediamine derivative is of value as agricultural chemical, particularly, as insecticide, because it is effective to block the transmission at neuromuscular junctions of insects in which glutamic acid serves as excitatory transmitter at their neuromuscular junctions, whereby decreasing actions of insects.

It has been further confirmed that the alkylene-diamine derivative of the invention is low both in acute toxicity and subacute toxicity.

In the aforementioned formulae (I) and (II), the aliphatic hydrocarbon group may be either saturated or unsaturated hydrocarbon group. However, saturated hydrocarbon group is preferred.

Each of $R^1$ and $R^6$ preferably is a straight or branched chain alkyl group having 3–8 carbon atoms such as propoyl, isopropyl, butyl, isobutyl, pentyl, isopentyl, hexyl, heptyl, octyl, or 2-ethylhexyl, or phenyl.

Each of $R^2$ and $R^7$ preferably is a straight or branched chain alkyl group having 4–8 carbon atoms such as butyl, isobutyl, pentyl, isopentyl, hexyl, heptyl, octyl, or 2-ethylhexyl. Otherwise, $R^2$ preferably is a straight or branched chain alkoxy group having 4–8 carbon atoms such as butoxy, isobutoxy, pentyloxy, isopentyloxy, hexyloxy, heptyloxy, octyloxy, or 2-ethylhexyloxy. Further, each of $R^2$ and $R^7$ preferably is a straight or branched chain aliphatic hydrocarbon group containing an ester bonding and 4–8 carbon atoms such as butyryloxypropyl, isobutyryloxyethyl, valeryloxyethyl, isovaleryloxyethyl, caproyloxyethyl or isocaproyloxyethyl. Furthermore, each of $R^2$ and $R^7$ preferably is an aliphatic hydrocarbon group containing an ether bonding and 4–8 carbon atoms such as isoproboxyethyl, isobutyloxy ether, isoproboxypropyl, pentyloxypropyl, or ixopentyloxyether, or phenyl group.

In the above forumla, "m" preferably is 0, 1 or 2 "n" preferably is 0, 1 or 2; "k" preferably is 1 or 2; each of "p" and "i" preferably is an integer of 2 to 6, more preferably is 2 or 3; and each of "q" and "j" preferably is 5.

Representative examples of the alkylenediamine derivatives of the invention are given below:

1-[3-[4-methyl-1-(3-methylbutyl)pentylamino]propyl]-piperidine;
1-[3-[4-methyl-1-(3-methylbutyl)pentylamino]propyl]-pyrrolidine;
1-[3-[4-methyl-1-(3-methylbutyl)pentylamino]propyl]-perhydroazepine;
1-[3-[4-methyl-1-(3-methylbutyl)pentylamino]propyl]-perhydroazocine
1-[2-[4-methyl-1-(3-methylbutyl)pentylamino]ethyl]-piperidine;
1-[4-[4-methyl-1-(3-methylbutyl)pentylamino]butyl]-piperidine;
1-[5-[4-methyl-1-(3-methylbutyl)pentylamino]pentyl]-piperidine;
1-[3-(1-pentylhexylamino)propyl]piperidine;
1-[3-[4,4-dimethyl-1-(3,3-dimethylbutyl)pentyl-amino]propyl]piperidine;
1-[3-[2,3-dimethyl-1-(3-methylbutyl)pentylamino]-propyl]piperidine;
1-[3-[1-(1-ethylpropyl)-4-methylpentylamino]propyl]-piperidine;
1-[3-[4-methyl-1-(2-phenylethyl)pentylamino]propyl]-piperidine;
1-[3-[4-methyl-1-(3-phenylpropyl)pentylamino]-propyl]piperidine;
1-[3-[5-methyl-2-(2-phenylethyl)hexylamino]propyl]-piperidine;
1-[3-(2benzyl-5-methylhexylamino)propyl]piperidine;
1-[3-(3-benzyl-6-methylheptylamino)propyl]piperidine;
1-[3-(6-methyl-3-phenylheptylamino)propyl]piperidine;
1-[3-[1-(3-methylbutyl)hexylamino]propyl]piperidine;
1-[3-[4,4-dimethyl-1-(3-methylbutyl)pentylamino]-propyl]piperidine;
1-[3-(1-benzyl-4-methylpentylamino)propyl]piperidine;
1-[3-(4-methyl-1-phenylpentylamino)propyl]piperidine;
1-[3-(5-methyl-2-phenylhexylamino)propyl]piperidine;
1-[3-(3-isopropoxy-1-phenylpropylamino)propyl]-piperidine;
1-[3-[2-(3-methylbutyloxy)-2-phenylethylamino]-propyl]piperidine;
1-[3-[2-phenylethylamino]propyl]piperidine;
3-phenyl-2-(3-piperidinopropylamino)propyl 3-methylbutanoate;
1-[3-(1-benzyl-4-methylpentylamino)propyl]pyrrolidine;
1-[3-(5-methyl-2-phenylhexylamino)propyl]pyrrolidine;
1-[3-(1-benzyl-4-methylpentylamino)propyl]perhydroazepine;
1-[2-(1-benzyl-4-methylpentylamino)ethyl]pyrrolidine;
1-[2-(1-benzyl-4-methylpentylamino)ethyl]piperidine;
1-[2-(4-methyl-1-(3-methylbutyl)pentylamino]ethyl]-piperidine;
1-[3-[bis(3-methylbutyl)amino]propyl]piperidine;
1-[3-[N-(3-methylbutyl)-N-(4-methylpentyl)amino]-propyl]piperidine;
1-[3-[N-(3-methylbutyl)-N-(5-methylhexyl)amino]-propyl]piperidine;
1-[3-[N-hexyl-N-(3-methylbutyl)amino]propyl]-piperidine;
1-[3-[N-heptyl-N-(3-methylbutyl)amino]propyl]-piperidine;
1-[3-[N-(3-methylbutyl)-N-octylamino]propyl]-piperidine;
1-[3-[N-(3-methylbutyl)-N-nonylamino]propyl]-piperidine;
1-[3-N-(3,3-dimethylbutyl)-N-(3-methylbutyl)amino]-propyl]piperidine;
1-[4-[N-(3-methylbutyl)-N-(5-methylhexyl)amino]-butyl]piperidine;
1-[2-[N-(3-methylbutyl)-N-(5-methylhexyl)amino]-ethyl]piperidine;
1-[3-[N-(3-methylbutyl)-N-(5-methylhexyl)amino]-propyl]pyrrolidine;
1-[3-[N-(3-methylbutyl)-N-(5-methylhexyl)amino]-propyl]perhydroazepine;
1-[3-[N,N-bis(3,3-dimethylbutyl)amino]propyl]-piperidine;
1-[3-[N-(2-benzyl-4-methylpentyl)-N-(3-methylbutyl)-amino]propyl]piperidine;
1-[7-[4-methyl-1-(3-methylbutyl)pentylamino]heptyl]-piperidine;
1-[7-[4-methyl-1-(3-methylbutyl)pentylamino]heptyl]-pyrrolidine;
1-[7-[4-methyl-1-(3-methylbutyl)pentylamino]heptyl]-perhydroazepine;

1-[7-[4-methyl-1-(3-methylbutyl)pentylamino]heptyl]-perhydroazocine
1-[8-[4-methyl-1-(3-methylbutyl)pentylamino]octyl]-piperidine;
1-[9-[4-methyl-1-(3-methylbutyl)pentylamino]nonyl]-piperidine;
1-[10-[4-methyl-1-(3-methylbutyl)pentylamino]decyl]-piperidine;
1-[7-(1-pentylhexylamino)heptyl]piperidine;
1-[7-[4-methyl-1-(2phenylethyl)pentylamino]heptyl]-piperidine;
1-[7-[4-methyl-1-(3-phenylpropyl)pentylamino]-heptyl]piperidine;
1-[7-[5-methyl-2-(2-phenylethyl)hexylamino]heptyl]-piperidine;
1-[7-(3-bentyl-6-methylheptylamino)heptyl]piperidine;
1-[7-(3-isopropoxy-1-phenylpropylamino]heptyl]-piperidine;
1-[7-[N,N-bis(3-methylbutyl)amino]heptyl]piperidine;
1-[7-[N-(3-methylbutyl)-N-(4-methylpentyl)amino]-heptyl]piperidine;
1-[7-[N-hexyl-N-(3-methylbutyl)amino]heptyl]-piperidine;
1-[7-[N,N-bis(3-methylbutyl)amino]heptyl]pyrrolidine;
1-[7-[N,N-bis(3-methylbutyl)amino]heptyl]perhydroazepine
1-[7-[N,N-bis(3-methylbutyl)amino]heptyl]perhydroazocine;
1-[7-[4-methyl-1-(3-methylbutyl)pentylamino]heptyl]-piperidinol;
1-[3-[N,N-bis(3-methylbutyl)amino]propyl]-4-piperidinol;
1-[3-[N,N-bis(3-methylbutyl)amino]propyl]-4-piperidinecarboxamide;
methyl 1-[3-[N,N-bis(3-methylbutyl)amino]propyl]-4-piperidinecarboxylate;
1-[3-[N,N-bis(3-methylbutyl)amino]propyl]-2,6-dimethylpiperidine;
1-[3-[N,N-bis(3-methylbutyl)amino]propyl]-1-piperidinemethanol;
1-[3-[N,N-bis(3-methylbutyl)amino]propyl]-3-methylpiperidine;
1-[3-[N,N-bis(3-methylbutyl)amino]propyl]-3-pyrrolidinol;
1-[3-[N,N-bis(3-methylbutyl)amino]propyl]-3-pyrrolidinecarboxamide;
methyl 1-[3-[N,N-bis(3-methylbutyl)amino]propyl]-2-pyrrolidinecarboxylate;
1-[3-N,N-bis(3-methylbutyl)amino]propyl]-2-methylpyrrolidine;
1-[3-[N,N-bis(3-methylbutyl)amino]propyl]-4-methylperhydroazepine;
1-[2-[N,N-bis(3-methylbutyl)amino]ethyl]-4-piperidinol;
1-[2-[N,N-bis(3-methylbutyl)amino]ethyl]-4-piperidinecarboxamide;
1-[3-[N-(3-methylbutyl)-N-(5-methylhexyl)amino]-propyl]-4-piperidinol;
1-[3-[N-(3-methylbutyl)-N-octylamino]propyl]-4-piperidinecarboxamide;
1-[3-[N-(3-methylbutyl)-N-nonylamino]propyl]-4-piperidinol;
1-[3-[N,N-bis(3,3-dimethylbutyl)amino]propyl]-2,6-dimethylpiperidine;
1-[3-[4-methyl-1-(3-methylbutyl)pentylamino]propyl]-4-piperidinol;
1-[3-[4-methyl-1-(3-methylbutyl)pentylamino]propyl]-4-piperidinecarboxamide;

methyl 1-[3-[4-methyl-1-(3-methylbutyl)pentylamino]-propyl]-4-piperidinecarboxylate;
2,6-dimethyl-1-[3-[4-methyl-1-(3-methylbutyl)pentyl-amino]propyl]piperidine;
1-[3-[4-methyl-1-(3-methylbutyl)pentylamino]propyl]-2-piperidinemethanol;
3-methyl-1-[3-[4-methyl-1-(3-methylbutyl)pentyl-amino]propyl]piperidine;
4-chloro-1-[3-[4-methyl-1-(3-methylbutyl)pentyl-amino]propyl]piperidine;
1-[3-[4-methyl-1-(3-methylbutyl)pentylamino]propyl]-4-nitropiperidine;
1-[3-[4-methyl-1-(3-methylbutyl)pentylamino]propyl]-3-pyrrolidinol;
1-[3-[4-methyl-1-(3-methylbutyl)pentylamino]propyl]-3-pyrrolidinecarboxamide;
methyl 1-[3-[4-methyl-1-(3-methylbutyl)pentylamino]-propyl]-4-pyrrolidinecarboxylate;
4-methyl-1-[3-[4-methyl-1-(3-methylbutyl)pentylamino]propyl]perhydroazepine;
1-[2-[4-methyl-1-(3-methylbutyl)pentylamino]ethyl]-4-piperidinol;
1-[2-[4-methyl-1-(3-methylbutyl)pentylamino]ethyl]-4-piperidinecarboxamide;
1-[3-[4-methyl-2-(3-methylbutyl)pentylamino]propyl]-4-piperidinol;
1-[3-(1-benzyl-4-methylpentylamino)propyl]-4-piperidinecarboxamide;
1-[3-(3-benzyl-6-methylheptylamino)propyl]-4-piperidinol;
2,6-dimethyl-1-[7-[4-methyl-1-(3-methylbutyl)pen-tylamino]heptyl]piperidine;
methyl 1-[7-[4-methyl-1-(3-methylbutyl)pentylamino]-heptyl]-4-piperidinecarboxylate;
1-[7-[4-methyl-1-(3-methylbutyl)pentylamino]heptyl]-piperidinecarboxamide;
1-[8-[N,N-bis(3-methylbutyl)amino]octyl]piperidine; and
1-[9-N,N-bis(3-methylbutyl)amino]nonyl]piperidine.

The alkylenediamine derivative of the invention is a compound wherein a heterocyclic group such as piperidinyl, pyrrolidinyl, perhydroazepinyl, perhydroazocinyl is attached to a carbon atom of an alkylamine via the nitrogen atom. Therefore, the alkylenediamine of the invention can form a salt with an optionally selected organic or inorganic acid. Examples of the organic acids include oxalic acid, fumaric acid, maleic acid, citric acid, tartaric acid, p-toluenesulfonic acid, and methanesulfonic acid. Examples of the inorganic acids include hydrochloric acid, sulfuric acid, nitric acid, hydrobromic acid, and phosphoric acid.

The alkylenediamine derivative of the invention can be employed in the form of a salt with any acid for the use as an insecticide, but ought to be in the form of a salt with a pharmaceutically acceptable acid. Examples of such acids include hydrochloric acid, fumaric acid, maleic acid, and methanesulfonic acid.

The alkylenediamine derivative of the formula (I) is a novel compound and can be prepared by, for example, following processes employing known compounds:

(1) a process employing reaction between amines having the formula:

$$R^1-(CH_2)_m-CH(R^2)-(CH_2)_n-NH_2$$

and a halide having the formula:

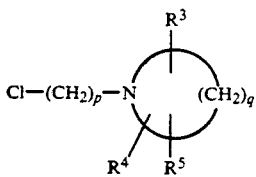

or (2) a process comprising steps of reacting a carboxylic acid having the formula:

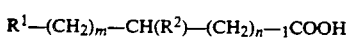

or its reactive derivative with an amine having the formula:

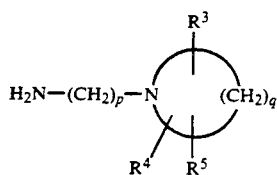

to obtain a compound having the formula:

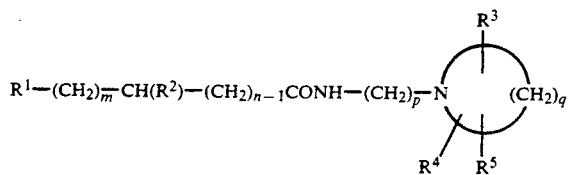

and reducing the obtained compound.

The alkylenediamine derivative of the formula (II) also is a novel compound and can be prepared by, for example, a process comprising steps of reacting a carboxylic acid or its reactive derivative having the formula:

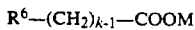

with an alkylenediamine compound having the formula:

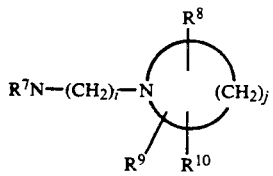

and reducing the reaction product.

The last-mentioned dialkylenediamine compound can be prepared from piperidine or pyridine having alkylamine and halogenized alkyl attached to N atom.

Details of these processes will be described hereinafter in synthesis examples of the specification. Compounds not described in each synthesis example can be prepared in the similar manner.

The alkylenediamine derivative of the invention can be employed as a pharmaceutical in various forms of conventional pharmaceutical compositions such as powder, granules, tablet, injection composition, and suppository.

The alkylenediamine derivative of the invention can be employed as a pharmaceutical for neuriatria at dosage of 0.1 to 50 mg/day in an injection composition and 1 to 500 mg/day in an orally adminiserable composition. However, the dosage can be varied depending on the age, conditions, and the like of the patient.

The alkylenediamine derivative of the invention can be employed as an insecticide for exterminating harmful insects in the form of a simple aqueous solution or in combination with additives generally employed for the preparation of agricultural chemicals. Such compositions can be as such employed with no dilution or can be used with additional water when it is actually used on the fields. Examples of the additives for agricultural chemicals include diluents (e.g., solvent, extender, filler, and carrier), surfactants (e.g., emusifying agent, and dispersing agent), stabilizers, and binders.

The present invention is further described by the following examples.

SYNTHESIS EXAMPLE 1

1-[3-(5-Methyl-2-phenylhexylamino)propyl]piperidine i) A mixture of 2.47 g of 5-methyl-2-phenylhexanoic acid and 1.43 g of thionyl chloride was stirred at room temperature for 27 hours, and subsequently excessive thionyl chloride was distilled off under reduced pressure at temperatures of lower than 40° C. The residue was dissolved in 5 ml of benzene. To the benzene solution was dropwise added under chilling with ice and viborous stirring over a period of 15 min. a mixture of 50 ml of 1 N aqueous sodium hydroxide and a solution of 1.42 g of 1-(3-aminopropyl)piperidine in 50 ml of chloroform. The stirring was continued for 30 min. under chilling with ice and for 40 min. at room temperature. The organic layer was separated and washed successively with water and saturated aqueous sodium chloride. The organic layer was then dried over anhydrous sodium sulfate and evaporated under reduced pressure to remove the solvent. There was obtained 3.0 g of 5-methyl-2-phenyl-N-(3-piperidinopropyl)hexanamide as a viscous oil, yield: 90.9%.

ii) To a solution of 3.0 g of the above-obtained product in 80 ml of ether was added 0.69 g of aluminum lithium hydride, and the resulting mixture was heated under reflux for 20 hours. To the reaction mixture was dropwise added under chilling with ice a saturated aqueous sodium sulfate solution to decompose an excessive portion of the aluminum lithium hydride. The insolubles were then removed by decantation. The organic layer was dried over anhydrous sodium sulfate and evaporated under reduced pressure to remove the solvent, yielding an oily product. The oily product was purified by silica gel column chromatography (eluent: chloroform-methanol) to give 2.6 g of the desired compound.

In a solution of the above-obtained free base in ethanol was dissolved fumaric acid of two-equivalent amount. The resulting solution was concentrated under reduced pressure to dryness, and the residue was recrystallized from ethanol to give a difumaric acid salt of the desired compound.

m.p.: 189°–192° C. (decompn.)

SYNTHESIS EXAMPLE 2

1-[3-(1-Pentylhexylamino)propyl]piperidine i) To a solution of 5.11 g of 6-undecanone in 20 ml of ethanol were successively added a solution of 3.47 g of hydroxylamine hydrochloride in 6 ml of water and a solution of 4.77 g of potassium hydroxide in 6 ml of water. The resulting mixture was heated under reflux for 3 hours. The reaction mixture was then poured into 150 ml of ice-containing water. The resulting aqueous mixture was made acidic by addition of 2 N hydrochloric acid, and extracted with benzene. The organic layer was washed with saturated aqueous sodium chloride and evaporated under reduced pressure to remove the solvent. There was obtained 5.57 g (corresponding to theoretical amount) of 6-undecanone oxime as a pale yellow solid, ii) To a solution of 1.85 g of the above-obtained product in 140 ml of ethanol was added 140 ml of 2 N aqueous sodium hydroxide and further added 10.7 g of Raney nickel at once. The resulting mixture was stirred for 1 hour, filtered, and washed successively with water and ethanol. The filtrate and the washings were combined, diluted with water, and then extracted with chloroform. The organic layer was washed with saturated aqueous sodium chloride and evaporated under reduced pressure to remove the solvent. There was obtained a pale yellow oil. This oil was purified by silica gel column chromatography (eluent; chloroform-methanol) to give 1.00 g of 6-undecanamine as a colorless oil, yield: 58.5%.

iii) A mixture of 0.85 g of the above-obtained product and 0.80 g of 1-(3-chloropropyl)piperidine was heated in a nitrogen atmosphere at 110°–120° C. for 3 hours. The reaction mixture was cooled and dissolved in ethanol. To the resulting solution was added 0.41 ml of conc. hydrochloric acid. The mixture was stirred, and then allowed to stand after addition of ethyl acetate. Thus precipitated crystals were collected by filtration, washed with ethyl acetate, and dried to give 640 mg of a crude crystalline product. The product was recrystallized from ethanol-ethyl acetate to give 540 mg of dihydrochloride of the desired compound as a white crystalline product, yield 29.5%.

m.p.: 233°–235° C.

SYNTHESIS EXAMPLE 3

1-[3-[4-Methyl-1-(3-methylbutyl)pentylamino]propyl]-piperidine i) To a solution of 5.11 g of 2,8-dimethylnonan-5-one (b.p.: 103°–105° C./19 mmHg, prepared by oxidizing 2,8-dimethylnonan-5-ol with a bleaching powder; 2,8-dimethylnonan-5-ol was prepared by reaction of ethyl formate and isoamylmagnesium bromide) in 20 ml of ethanol were successively added an aqueous solution of 3.47 of hydroxylamine hydrochloride in 6 ml of water and a solution of 4.77 g of potassium hydroxide in 6 ml of water. The mixture was heated under reflux. The reaction mixture was then poured into 150 ml of ice-containing water. The aqueous mixture was made acidic by addition of 2 N hydrochloric acid and extracted with benzene. The organic layer was washed with saturated aqueous sodium chloride, dried over anhydrous sodium sulfate, and evaporated under reduced pressure to remove the solvent. There was obtained 5.21 g of 2,8-dimethylnonan-5-one oxime as a pale brown oil, yield: 93.7%.

ii) To a solution of 2.78 g of the above-obtained product in 60 ml of ethanol was added 60 ml of 2 N aqueous sodium hydroxide and further added 4.32 g of Raney alloy at once. The resulting mixture was stirred for 3 hour, filtered, and washed successively with ethanol and water. The filtrate and the washings were combined, diluted with water, and then extracted with chloroform. The extract was dried over anhydrous sodium sulfate and evaporated under reduced pressure to remove the solvent. There was obtained a crude product containing 2,8-dimethylnonan-5-amine. This was then isolated in the form of an oxalate. The oxalate was treated with aqueous sodium hydroxide to give a free base.

iii) A mixture of 1.55 g of the above-obtained product and 1-(3-chloropropyl)piperidine was heated to 120° C. for 3.5 hours in a nitrogen atmosphere. The reaction mixture was cooled and dissolved in 10 ml of ethanol. To this solution was added 0.75 ml of conc. hydrochloric acid and ethyl acetate of a volume to make the total volume to 100 ml. The precipitated crystals were collected by filtration. The crystals were treated with aqueous sodium hydroxide and extracted with chloroform to obtain an oil. The oil was purified by silica gel column chromatography (eluent: chloroform-methanol) to give the desired compound as an oil.

To an ethanol solution containing the above-obtained free base was added a slightly excessive amount of 6 N hydrochloric acid-ethanol. The mixture was concentrated to dryness. The residue was recrystallized from ethanol-ethyl acetate to give dihydrochloride of the desired compound as a white crystalline product.

m.p.: 249°–250° C. (decompn.)

SYNTHESIS EXAMPLES 4-25

Essentially according to the processes of the above synthesis examples, the following compounds were prepared.

| Syn Ex. No. | |
|---|---|
| 4 | 1-[3-(1-Benzyl-4-methylpentylamino)propyl]-piperidine, m.p. 228–231° C. (decompn., as dihydrochloride) |
| 5 | 1-[3-(4-Methyl-1-phenylpentylamino)propyl]-piperidine, m.p. 211–215° C. (decompn., as dihydrochloride) |
| 6 | 1-[3-(3-Isopropoxy-1-phenylpropylamino)propyl]-piperidine, m.p. 199–201° C. (decompn., as dihydrochloride) |
| 7 | 1-[3-[2-(3-Methylbutyloxy-2-phenylethylamino)-propyl]piperidine, m.p. 198–199° C. (as dihydrochloride) |
| 8 | 1-[3-(2-Phenoxy-2-phenylethylamino)propyl]-piperidine, m.p. 243–244° C. (decompn., as dihydrochloride) |
| 9 | 3-Phenyl-2-(3-piperidinopropylamino)propyl 3-methylbutanoate, m.p. 189–190° C. (decompn., as dihydrochloride) |
| 10 | 1-[3-[4-Methyl-1-(2-phenylethyl)pentylamino]-propyl]piperidine, m.p. 220–223° C. (decompn., as dihydrochloride) |
| 11 | 1-[3-(3-Benzyl-6-methylheptylamino)propyl]-piperidine, m.p. 229–233° C. (decompn., as dihydrochloride) |
| 12 | 1-[3-(2-Benzyl-5-methylhexylamino)propyl]-piperidine, m.p. 228–230° C. (decompn., as dihydrochloride) |
| 13 | 1-[3-[4-Methyl-1-(3-phenylpropyl)pentylamino]-propyl]piperidine, m.p. 181–181.5° C. (decompn., as dihydrochloride) |
| 14 | 1-[3-[2,3-Dimethyl-1-(3-methylbutyl)pentyl-amino]propyl]piperidine, m.p. 179–181° C. (decompn., as difumarate) |

| Syn Ex. No. | |
|---|---|
| 15 | 1-[3-[1-(1-Ethylpropyl)-4-methylpentylamino]propyl]piperidine, m.p. 210–212° C. (decompn., as dihydrochloride) |
| 16 | 1-[3-(6-Methyl-3-phenylheptylamino)propyl]piperidine, m.p. 173–176° C. (decompn., as difumarate) |
| 17 | 1-[3-[4,4-Dimethyl-1-(3,3-dimethylbutyl)pentylamino]propyl]piperidine, m.p. 282–284° C. (decompn., as dihydrochloride) |
| 18 | 1-[3-[1-(3-Methylbutyl)hexylamino]propyl]piperidine, m.p. 233–236° C. (decompn., as dihydrochloride) |
| 19 | 1-[3-[4,4-Dimethyl-1-(3-methylbutyl)pentylamino]propyl]piperidine, m.p. 256–263° C. (decompn., as dihydrochloride) |
| 20 | 1-[3-[4-methyl-1-(3-methylbutyl)pentylamino]propyl]pyrrolidine, m.p. 248–250° C. (decompn., as dihydrochloride) |
| 21 | 1-[3-[4-Methyl-1-(3-methylbutyl)pentylamino]propyl]perhydroazepine, m.p. 220–226° C. (decompn., as dihydrochloride) |
| 22 | 1-[3-[4-Methyl-1-(3-methylbutyl)pentylamino]propyl]perhydroazocine, m.p. 196–198° C. (decompn., as dihydrochloride) |
| 23 | 1-[2-[4-Methyl-1-(3-methylbutyl)pentylamino]ethyl]piperidine, m.p. 261–263° C. (decompn., as dihydrochloride) |
| 24 | 1-[4-(4-Methyl-2-(3-methylbutyl)pentylamino]butyl]piperidine, m.p. 263–266° C. (decompn., as dihydrochloride) |
| 25 | 1-[5-[4-Methyl-1-(3-methylbutyl)pentylamino]pentyl]piperidine, m.p. 225–227° C. (decompn., as dihydrochloride) |

SYNTHESIS EXAMPLE 26

1-[3-[N,N-Bis-(3-methylbutyl)amino]propyl]piperidine i) A mixture of 23.2 ml of isoamylamine and 16.17 g of 1-(3-chloropropyl)piperidine was heated to 120° C. for 2 hours. The reaction mixture was then dissolved in 100 ml of ethanol. To this ethanol solution was added 17 ml of conc. hydrochloric acid. The mixture was allowed to stand overnight at room temperature. The precipitated crystals were collected, washed with ethanol, and dried to give 14.70 g of 1-[3-(3-methylbutylamino)propyl]piperidine dihydrochloride as a white crystalline product.

The motor liquor was concentrated to dryness, and the residue was recrystallized from 50 ml of ethanol to further obtain 3.64 g of the white crystalline product, yield 64%. m.p.: 263°–265° C. (decompn.)

ii) A mixture of 1.43 g of the above-obtained product, 20 ml of chloroform, and 24 ml of aqueous sodium hydroxide was stirred at room temperature. When the reaction mixture turned transparent, the mixture was chilled with ice. To the chilled mixture was dropwise added 1.21 g of isovaleroyl chloride. The mixture was then stirred for 30 min. under chilling with ice and for 1 hour at room temperature. The organic layer was separated and washed successively with 2 N aqueous sodium hydroxide and saturated aqueous sodium chloride. The washed product was then dried over anhydrous sodium sulfate and evaporated to remove the solvent. There was obtained 1.46 g of N-(3-methylbutyl)-N-(3-piperidinopropyl)-3-methylbutanamide as crude crystals.

iii) In 10 ml of tetrahydrofuran was suspended 0.76 g of lithium aluminum hydride, and this suspension was chilled with ice. To this suspension was dropwise added a solution of 1.46 g of the above-obtained product in 20 ml of tetrahydrofuran. The reaction mixture was heated under reflux for one hour, and then chilled with ice. To the chilled mixture was added successively ethyl acetate and saturated aqueous ammonium chloride to decompose an excessive portion of lithium aluminum hydride. The organic layer was recovered by decantation. The organic layer was washed with saturated aqueous sodium sulfate, dried over anhydrous sodium sulfate and evaporated under reduced pressure to remove the solvent. The residue was purified by silica gel column chromatography (eluent: chloroform-methanol) to give 0.81 g of the desired compound as a pale yellow oil, yield: 57%.

To an ethanol solution containing 0.81 g of the above-obtained product was added an excessive amount of hydrochloric acid-ethanol, and the mixture was concentrated under reduced pressure to dryness. The residue was recrystallized from acetone to give 0.78 g of dihydrochloride of the desired compound as a white crystalline product, yield: 76%.

m.p.: 182°–184° C. (decompn.)

SYNTHESIS EXAMPLE 27

1-[3-[N-(3-Methylbutyl)-N-(4-methylpentyl)amino]propyl]piperidine i) In the similar manner to the manner as in Synthesis Example 26, 1.09 g of 4-methyl-N-(3-methylbutyl)-N-(3-piperidinopropyl)pentanamide was prepared from 1.00 g of 1-[3-(3-methylbutylamino)propyl]piperidine dihydrochloride and 0.95 g of 4-methylpentanoyl chloride.

ii) In 10 ml of dry ether was suspended 0.53 g of lithium aluminum hydride. The resulting suspension was dropwise added to a solution of 1.09 g of the above-obtained product in 15 ml of ether. After the addition was complete, the mixture was stirred at room temperature for one hour and again chilled with ice. To the chilled mixture was added ethyl acetate to decompose an excessive portion of lithium aluminum hydride. To the mixture was then added a saturated aqueous sodium sulfate, and the organic layer was separated by decantation. The organic layer was dried over anhydrous sodium sulfate, evaporated under reduced pressure to remove the solvent. The residue was purified by silica gel column chromatography (eluent: chloroform-methanol) to give 600 mg of the desired compound as a colorless oil, yield 64%.

The the above free base in ethanol was added two-equivalent amount (0.52 g) of fumaric acid. The mixture was heated to make a solution. To the mixture was then added ethyl acetate, and it was allowed to stand overnight. The precipitated crystals were collected by filtration, washed successively with ethyl acetate and hexane, and dried to give 0.95 g of difumarate of the desired compound as a white crystalline product, yield: 51%.

m.p.: 138°–140° C.

SYNTHESIS EXAMPLES 28–42

Essentially according to the processes of the above synthesis examples, the following compounds were prepared.

| Syn Ex. No. | |
|---|---|
| 28 | 1-[3-[3-Methyl-N-(2-phenoxyethyl)butylamino]propyl]piperidine, m.p. 117–119° C. (decompn., as dihydrochloride) |
| 29 | 1-[3-[3-Methyl-N-(2-phenylethyl)butylamino]propyl]piperidine, m.p. 144–146° C. (decompn., |

-continued

| Syn Ex. No. | |
|---|---|
| | as difumarate) |
| 30 | 1-[3-[3-Methyl-N-(3-phenylpropyl)butylamino]-propyl]piperidine, m.p. 117–119° C. (decompn., as difumarate) |
| 31 | 1-[3-[3-Methyl-N-(4-phenylbutyl)butylamino]-propyl]piperidine, m.p. 112–114° C. (decompn., as difumarate) |
| 32 | 1-[3-[N-(3-Methylbutyl)-N-(5-methylhexyl)-amino]propyl]piperidine, m.p. 139–141° C. (decompn., as difumarate) |
| 33 | 1-[3-[N-hexyl-N-(3-methylbutyl)amino]propyl]-piperidine, m.p. 138–139° C. (as difumarate) |
| 34 | 1-[3-[N-heptyl-N-(3-methylbutyl)amino]propyl]-piperidine, m.p. 132–134° C. (decompn. as difumarate) |
| 35 | 1-[3-[N-(3-Methylbutyl)-N-octyl)amino]propyl]-piperidine, m.p. 127–131° C. (decompn., as difumarate) |
| 36 | 1-[3-[N-(3-Methylbutyl)-N-nonyl)amino]propyl]-piperidine, m.p. 136–138° C. (decompn., as difumarate) |
| 37 | 1-[3-[N-(3,3-Dimethylbutyl)-N-(3-methylbutyl)-amino]propyl]piperidine, m.p. 152–154° C. (decompn., as difumarate) |
| 38 | 1-[4-[N-(3-Methylbutyl)-N-(5-methylhexyl)-amino]butyl]piperidine, m.p. 130° C. (as difumarate) |
| 39 | 1-[2-[N-(3-Methylbutyl)-N-(5-methylhexyl)-amino]ethyl]piperidine, m.p. 140–141° C. (decompn., as difumarate) |
| 40 | 1-[2-[N-(3-Methylbutyl)-N-(5-methylhexyl)-amino]propyl]pyrrolidine, m.p. 134–135° C. (as difumarate) |
| 41 | 1-[3-[N-(3-Methylbutyl)-N-(5-methylhexyl)-amino]propyl]perhydroazepin, m.p. 128.5–131.5° C. (as difumarate) |
| 42 | 1-[3-[N,N-Bis(2,3-dimethybutyl)amino]propyl]-piperidine, m.p. 159–163° C. (decompn., as difumarate) |

SYNTHESIS EXAMPLE 43

1-[7-[4-Methyl-1-(3-methylbutyl)pentylamino]heptyl]-piperidine i) In a flask equipped with a dropping funnel and a cooler was placed a mixture of 8.94 g of piperidine, 7.7 ml of benzene and 1.5 ml of chloroform. The mixture was refluxed by heating, and to the mixture was dropwise added 9.50 g of 7-bromoheptanenitrile. After the addition was complete, the mixture was further refluxed by heating for 4 hours and then cooled under ambient condition. To the mixture was added ether, and the resulting mixture was stirred for a while. The reaction mixture was filtered to remove insolubles. The insolubles were washed with ether. The filtrate and washings were combined and concentrated under reduced pressure. The residue was distilled under reduced pressure to give 7-piperidinoheptanenitrile as a colorless oil, yield: 8.92 g (theoretical yield).

b.p.: 113°–115° C./2 mmHg ii) To a solution of 7.77 g of the above-obtained product in 30 ml of ether was dropwise added under chilling with ice 1.82 g of aluminum lithium hydride. After the addition was complete, the resulting mixture was warmed to room temperature over 2 hours and then stirred overnight. To the reaction mixture was dropwise added under chilling with ice a saturated aqueous sodium sulfate solution to decompose an excessive portion of the aluminum lithium hydride. To the mixture were added ether and anhydrous sodium sulfate, and insolubles were removed by filtration. The filtrate was concentrated under reduced pressure, and the residue was distilled under reduced pressure to give 1-(7-aminoheptyl)piperidine as a colorless oil, yield: 5.39 g (68%).

b.p.: 106°–107° C./2.5 mmHg (iii) To a solution of 1.70 g of 2,8-dimethylnonan-5-one and 1.98 g of 1-(7-aminoheptyl)piperidine in 50 ml of methanol was added 6 N hydrochloric acid-ethanol to have a pH value of approx. 7 (pH test paper). To the resulting solution was added under cooling 1.26 g of sodium borohydride all at once. The resulting mixture was stirred under chilling with ice for one hour, and then stirred overnight at room temperature. The reaction mixture was concentrated, and the residue was extracted with chloroform after addition of water and an aqueous sodium hydroxide solution. The chloroform portion was dried and evaporated under reduced pressure to remove the solvent, yielding an oily product. The oil product was purified by silica gel column chromatography (eluent: chloroform-methanol 80:1 to 40:1) to give the desired compound as a colorless oil.

To a solution of the obtained compound in ethanol was added 6 N hydrochloric acid-ethanol, and the mixture was concentrated under reduced pressure. The residual white solid was recrystallized from ethanol-ethyl acetate to give hydrochloride of the desired compound as a white crystalline product, yield: 330 mg (16%).

m.p.: 189°–190° C.

SYNTHESIS EXAMPLES 44–49

Essentially according to the processes of Synthesis Examples 1–3, the following compounds were prepared.

| Syn Ex. No. | |
|---|---|
| 44 | 1-[3-[N,N-Bis(3-methylbutyl)amino]propyl]-4-piperidinol, m.p. 155–157° C. (as dihydrochloride) |
| 45 | 1-[3-[N,N-Bis(3-methylbutyl)amino]propyl]-4-piperidinecarboxamide, m.p. 150–152° C. (as dihydrochloride) |
| 46 | Methyl 1-[3-[N,N-bis(3-methylbutyl)amino]-propyl]-2-pyrrolidinecarboxylate, pale yellow oil |
| 47 | 1-[3-[N,N-Bis(3-methylbutyl)amino]propyl]-2,6-dimethylpiperidine, yellow oil; m.p. 137–139° C. (as 3/2 fumarate) |
| 48 | 1-[3-[4-Methyl-1-(3-methylbutyl)pentylamino]-propyl]-2-piperidinemethanol, m.p. 192–194° C. (as dihydrochloride) |
| 49 | 3-Methyl-1-[3-[4-methyl-1-(3-methylbutyl)-pentylamino]propyl]piperidine, m.p. 195–197° C. (decompn., as dihydrochloride) |

REFERENCE EXAMPLES

Glutamate Blocking Effect on Neuromuscular Junction of Crayfish (1) Evaluation of glutamate blocking effect was performed according to the methods of Ishida et al [J. Physiol., 298, 301–319(1980)], and Shinozaki et al[Comp. Biochem. Physiol, 70c, 49–58(1981)]. In more detail, the opener muscle of the first walking leg of the crayfish is employed for the examination described below.

A neuromuscular sample is fixed in a vessel, and an aqueous salt solution for crayfish [composition: NaCl (195 mM), $CaCl_2$ (18 mM), KCl (5.4 mM), Tris-maleate buffer (pH 7.5, 10 mM), and glucose (11 mM)] was circulated at a constant rate into the vessel.

A glass microelectrode filled with 3 M KCl solution was inserted into the middle portion of the muscle fibre and the change of potential induced by L-glutamate ($1 \times 10^{-4}$ M) was measured intracellularly.

The glutamate blocking effect of the compound to be tested was evaluated by determining an inhibition ratio of glutamate potential pretreated by the test solution ($2 \times 10^{-5}$ M) for 5 min.

The results are set forth in Table 1.

TABLE 1

| Compound Tested | Glutamate Blocking Effect |
|---|---|
| Synthesis Example 1 | 99% |
| Synthesis Example 2 | 80% |
| Synthesis Example 3 | 99% |
| Synthesis Example 4 | 99% |
| Synthesis Examples 5–6 | 94% |
| Synthesis Example 7 | 96% |
| Synthesis Example 8 | 94% |
| Synthesis Example 9 | 90% |
| Synthesis Example 10 | 99% |
| Synthesis Example 11 | 96% |
| Synthesis Example 12 | 98% |
| Synthesis Example 13 | 96% |
| Synthesis Example 15 | 94% |
| Synthesis Example 18 | 97% |
| Synthesis Example 19 | 88% |
| Synthesis Example 20 | 96% |
| Synthesis Examples 21–25 | 100% |
| Synthesis Example 26 | 91% |
| Synthesis Example 28 | 72% |
| Synthesis Example 29 | 80% |
| Synthesis Example 30 | 96% |
| Synthesis Example 33 | 83% |
| Synthesis Example 34 | 91% |
| Synthesis Examples 35–36 | 94% |
| Synthesis Example 38 | 96% |
| Synthesis Example 40 | 94% |
| Synthesis Example 41 | 100% |
| Synthesis Example 43 | 74% |
| Synthesis Example 44 | 71% |

(2) The glutamate blocking effects of the compound of the present invention as described in Synthesis Example 3 (i.e. 1-[3-[4-methyl-1-(3-methylbutyl)pentylamino]-propyl]piperidine) and the known 5-methyl-1-phenyl-2-(3-piperidinopropylamino)hexan-1-ol were evaluated in the same manner as above except that the concentration of the liquid for the pretreatment was reduced from $2 \times 10^{-5}$ M to $5 \times 10^{-7}$ M. The results are set forth in Table 2.

TABLE 2

| Compound Tested | Glutamate Blocking Effect |
|---|---|
| 1-[3-[4-Methyl-1-(3-methylbutyl)-pentylamino]propyl]piperidine (according to the invention) | 25% |
| 5-Methyl-1-phenyl-2-(3-piperidinopropylamino)hexan-1-ol (for comparison) | 6% |

(3) The neuromuscular sample which was fixed in the vessel and treated in the above manner was subsequently washed with the salt solution flowing in the vessel under circulation for 40 min. After such washing was complete, the glutamate response was measured on the washed neuromuscular sample.

It was confirmed that the sample treated with 5-methyl-1-phenyl-2-(3-piperidinopropylamino)hexan-1-ol showed a glutamate response at almost the same level as shown by the sample prior to the treatment. Accordingly, it was confirmed that the glutamate blocking action of the aninoalcohol derivative was not kept for sufficient period of time. In contrast, 1-[3-[4-methyl-1-(3-methyl-butyl)pentylamino]propyl]piperidine of the invention showed almost no glutamate response even after it was well washed with the salt solution. The prolongation of the effect of glutamate response shown in using this alkylenediamine compound was also observed on the alkylenediamine compound was also observed on the alkylenediamine derivatives tested in the (1) above.

(4) Acute toxicity ($LD_{50}$, i.v.) was measured on the alkylenediamine derivatives of the invention and the known aminoalcohol derivative. The results are set forth in Table 3.

TABLE 3

| Compound Tested | Acute Toxicity ($LD_{50}$) |
|---|---|
| 1-[3-(1-Pentylhexylamino)propyl]piperidine | 23.3 mg/kg |
| 1-[3-[4-Methyl-1-(3-methylbutyl)-pentylamino]propyl]piperidine | 29.5 mg/kg |
| 1-[3-[N,N-Bis(3-methylbutyl)amino]propyl]piperidine | 24.8 mg/kg |
| 5-Methyl-1-phenyl-2-(3-piperidinopropylamino)hexan-1-ol | 13.6 mg/kg |

It is apparent that the alkylenediamine derivatives of the invention show less accute toxicity than the known aminoalcohol derivative.

We claim:

1. An alkylenediamine derivative having the formula:

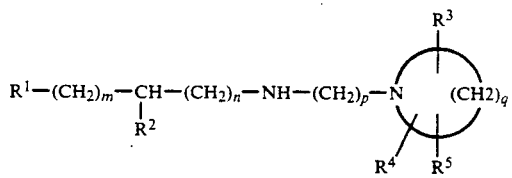

wherein $R^1$ is a straight or branched chain alkyl group containing 3–8 carbon atoms, an alicyclic hydrocarbon group containing 5–8 carbon atoms, an aryl group, or an aralkyl group having an alkyl group containing 1–4 carbon atoms; $R^2$ is a straight or branched chain alkyl group containing 3–11 carbon atoms, an alkoxy group containing 3–11 carbon atoms, an aliphatic hydrocarbon group containing an ester bonding and 3–11 carbon atoms, an aliphatic hydrocarbon group containing an ether bonding and 3–11 carbon atoms, or an aryloxy group; each of $R^3$, $R^4$ and $R^5$ is hydrogen; and each of m and n is an integer of 0 to 3, provided that m+n does not exceed 3; p is an integer of 2 to 13; and q is an integer of 4 to 7.

2. The alkylenediamine derivative claimed in claim 1, wherein $R^1$ is a straight or branched chain alkyl group having 3–8 carbon atoms or phenyl.

3. The alkylenediamine derivative as claimed in claim 1, wherein $R^2$ is a straight or branched chain alkyl group having 4–8 carbon atoms, alkoxy group having 4–8 carbon atoms, aliphatic hydrocarbon group containing an ester bonding and 4–8 carbon atoms, aliphatic hydrocarbon group containing an ether bonding and 4–8 carbon atoms or phenoxy group.

4. The alkylenediamine derivative as claimed in claim 1, wherein m is 0, 1 or 2.

5. The alkylenediamine derivative as claimed in claim 1, wherein n is 0, 1 or 2.

6. The alkylenediamine derivative as claimed in claim 1, wherein p is an integer of 2 to 6.

7. The alkylenediamine derivative as claimed in claim 1, wherein p is 2 or 3.

8. The alkylenediamine derivative as claimed in claim 1, wherein q is 5.

9. An alkylenediamine derivative having the formula:

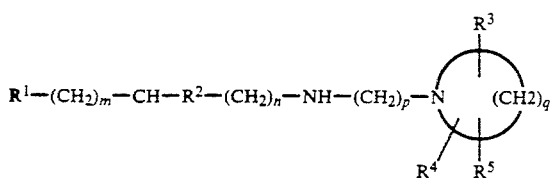

wherein $R^1$ is a straight or branched chain alkyl group containing 3-8 carbon atoms, an alicyclic hydrocarbon group containing 5-8 carbon atoms, an aryl group, or an aralkyl group having an alkyl group containing 1-4 carbon atoms; $R^2$ is a straight or branched chain alkyl group containing 3-11 carbon atoms, an alkoxy group containing 3-11 carbon atoms, an aliphatic hydrocarbon group containing an ester bonding and 3-11 carbon atoms, an aliphatic hydrocarbon group containing an ether bonding and 3-11 carbon atoms, or an aryloxy group; each of $R^3$, $R^4$ and $R^5$ independently is hydrogen, a saturated or unsaturated straight or branched chain alkyl group containing 1-6 carbon atoms, an alkoxy group containing 1-6 carbon atoms, an acyloxy group containing 1-6 carbon atoms, an aryl group which may have at least one substituent, an aralkyl group having an alkyl group of 1-5 carbon atoms which may have at least one substituent, hydroxyl, a hydroxylalkyl group having an alkyl group of 1-3 carbon atoms, halogen, nitrile, nitro, amino, carbamoyl, or alkoxycarbonyl having an alkyl group of 1-5 carbon atoms, provided that there is no case where $R^3$, $R^4$ and $R^5$ all are hydrogens; and each of m and n is an integer of 0 to 3, provided that m+n does not exceed 3; p is an integer of 2 to 13; and q is an integer of 4 to 7.

10. The alkylenediamine derivative claimed in claim 9, wherein $R^1$ is a straight or branched chain alkyl group having 3-8 carbon atoms or phenyl.

11. The alkylenediamine derivative as claimed in claim 9, wherein $R^2$ is a straight or branched chain alkyl group having 4-8 carbon atoms, alkoxy group having 4-8 carbon atoms, aliphatic hydrocarbon group containing an ester bonding and 4-8 carbon atoms, aliphatic hydrocarbon group containing an ether bonding and 4-8 carbon atoms or phenoxy group.

12. The alkylenediamine derivative as claimed in claim 9, wherein m is 0, 1 or 2.

13. The alkylenediamine derivative as claimed in claim 9, wherein n is 0, 1 or 2.

14. The alkylenediamine derivative as claimed in claim 9, wherein p is an integer of 2 to 6.

15. The alkylenediamine derivative as claimed in claim 9, wherein p is 2 or 3.

16. The alkylenediamine derivative as claimed in claim 9, wherein q is 5.

17. The alklenediamine derivative as claimed in claim 1, wherein p is 2 or 3.

* * * * *